United States Patent [19]

Metzner et al.

[11] Patent Number: 5,308,859
[45] Date of Patent: May 3, 1994

[54] COMPOSITION FOR PRESERVATION OF WOOD AND WOOD-BASED MATERIALS

[75] Inventors: Wolfgang Metzner; Rainer Gruening, both of Krefeld, Fed. Rep. of Germany

[73] Assignee: Deutsche Solvay-Werke GmbH, Solingen, Fed. Rep. of Germany

[21] Appl. No.: 780,539

[22] Filed: Oct. 21, 1991

Related U.S. Application Data

[63] Continuation of Ser. No. 127,977, Dec. 3, 1987, abandoned.

[30] Foreign Application Priority Data

Dec. 5, 1986 [DE] Fed. Rep. of Germany ....... 3641555

[51] Int. Cl.$^5$ ............................................. A01N 43/64
[52] U.S. Cl. ................................... 514/383; 106/15.05; 252/399; 514/521
[58] Field of Search ............... 514/383, 359, 397, 396, 514/521; 106/15.05; 252/399

[56] References Cited

U.S. PATENT DOCUMENTS

| | | | |
|---|---|---|---|
| 4,542,146 | 9/1985 | Van Gestel; et al. | 514/383 |
| 4,661,382 | 4/1987 | Cooke, Jr. | 427/297 |

FOREIGN PATENT DOCUMENTS

| | | |
|---|---|---|
| 0050738 | 5/1982 | European Pat. Off. . |
| 0148526 | 7/1985 | European Pat. Off. . |
| 0198165 | 10/1986 | European Pat. Off. . |
| 2709264 | 9/1978 | Fed. Rep. of Germany . |
| 2551560 | 4/1981 | Fed. Rep. of Germany . |
| 3414244A1 | 10/1985 | Fed. Rep. of Germany . |

OTHER PUBLICATIONS

Derwent Abstract Accession No. 77-61388Y/35, German Patent No. 2607031, Aug. 25, 1977.
Chemical Abstract, vol. 102, No. 74219z, Japanese patent no. 84,115,805, Jul. 4, 1984.

*Primary Examiner*—Amelia Burgess Yarbrough
*Attorney, Agent, or Firm*—Foley & Lardner

[57] ABSTRACT

A composition for preservation of wood and wood-based materials, comprising 0.001%–5% by weight of 1-[[2-(2,4-dichlorophenyl)-1,3-dioxolan-2-yl]methyl]-1H-1,2,4-triazole, 0.001%–3% by weight, of at least one of cyano-(4-fluoro-3-phenoxyphenyl)-methyl-3-(2,2-dichloroethenyl)-2,2-dimethylcyclopropylcarboxylate, ((pentafluorophenyl)-methyl)-1R,3R-3-(2,2-dichloroethenyl)-2,2-dimethylcyclopropylcarboxylate, methylbisthiocyanate, and N,N-dimethyl-N′-phenyl-N′-(fluorodichloromethyltolyl-N′-(dichlorofluoromethylthio)sulfamide and suspending agent comprising at least one of a diluent, an emulsifier, and a wetting agent, is provided together with a process for preparing such compositions.

23 Claims, No Drawings

COMPOSITION FOR PRESERVATION OF WOOD AND WOOD-BASED MATERIALS

This application is a continuation of application Ser. No. 127,977, filed Dec. 3, 1987, now abandoned.

BACKGROUND OF THE INVENTION

The present invention relates to a composition for preservation of wood and wood-based materials comprising 1-[[2-(2,4-dichloro-phenyl)-1,3-dioxolan-2-yl]methyl]-1H-1,2,4-triazole and at least one compound selected from the group consisting of (i) cyano-(4-fluoro-3-phenoxyphenyl)-methyl-3-(2,2-dichloroethenyl)-2,2-dimethylcyclopropylcarboxylate, (ii) ((pentafluorophenyl)-methyl)-1R,3R-3-(2,2-dichloroethenyl)-2,2-dimethylcyclopropylcarboxylate, (iii) methyl-bisthiocyanate, (iv) N,N-dimethyl-N'-phenyl-N'-(fluorodichloromethyl-thio)sulfamide, and (v) N,N-dimethyl-N'-p-tolyl-N'-(dichlorofluoromethylthio)sulfamide. Optionally, the composition further comprises at least one of the group consisting of one other insecticide, a processing auxiliary, a processing additive, an organic chemical binding agent, a fixative, a dye, and a pigment.

This invention also relates to a process for preparation of a composition for preservation of wood and wood-based materials.

The chemical compound 1-[[2-(2,4-dichlorophenyl)-1,3-dioxolan-2-yl]methyl]-1H-1,2,4-triazole ("azaconazole") having the structural formula

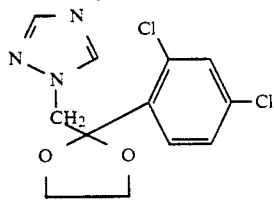

is known and has been described in German Patent No. 2,551,560 as a fungicidal and plant growth regulatory agent for agricultural use. Requirements placed on wood preserving agents, however, are considerably different from those placed on fungicides for plant protection.

The chemical compounds cyano-(4-fluoro-3-phenoxyphenyl)-methyl-3-(2,2-dichloroethenyl)-2,2-dimethylcyclopropylcarboxylate and ((pentafluorophenyl)-methyl)-1R,3R-3-(2,2-dichloroethenyl)-2,2-dimethylcyclopropylcarboxylate are known and have been described in German Offenlegungsschrift 2,709,264 as insecticides for plant protection. However these insecticides do not comply with the requirements with regard to resistance to aging and resistance against atmospheric influences which are placed on wood preservatives.

The object of the present invention is, therefore, to find a wood preservative which is highly active against wood-discoloring and wood-destroying fungi and also against wood-damaging insects, particularly against termites, and which exhibits a good long-term action, wherein the activity of the fungicide is not impaired by the insecticide or vice versa. Moreover, this wood preservative should exhibit good penetrating power in wood and in wood-based materials.

SUMMARY OF THE INVENTION

In accomplishing these and other objects, there has been provided in accordance with one aspect of the present invention, a composition for preservation of wood or wood-based materials comprising a predetermined amount of each of components (a) a compound 1-[[2-(2,4-dichlorophenyl)-1,3-dioxolan-2-yl]methyl]-1H-1,2,4-triazole, (b) at least one compound selected from the group consisting of
  (i) cyano-(4-fluoro-3-phenoxyphenyl)-methyl-3-(2,2-dichloroethenyl)-2,2-dimethylcyclopropylcarboxylate,
  (ii) ((pentafluorophenyl)-methyl)-1R,3R-3- (2,2-dichloroethenyl)-2,2-dimethylcyclopropyl-carboxylate,
  (iii) methyl-bisthiocyanate,
  (iv) N,N-dimethyl-N'-phenyl-N'-(fluorodichloromethyl-thio)sulfamide,
  (v) N,N-dimethyl-N'-p-tolyl-N'(dichlorofluoromethylthio)-sulfamide, and (c) a suspending agent that comprises at least one of a diluent, an emulsifier and a wetting agent.

In accordance with another aspect of the present invention, there has been provided a composition as described above, wherein the composition further comprises an amount of at least one of components
  (d) a binding agent,
  (e) a fixative, and
  (f) a plasticizer.

In accordance with yet another aspect of the present invention, there has been provided a composition as described above, wherein amounts of components (a)-(c) are present in a mixture with an amount of at least one of components
  (d) an organic binding agent,
  (e) a fixative, and
  (f) a plasticizer.

In accordance with still another aspect of the present invention, there has been provided a composition as described above, wherein the composition further comprises a predetermined amount of each of components
  (g) at least one other biocide soluble in the diluent, and
  (h) at least one of a water-soluble or water-insoluble dye, a color pigment, an anti-corrosive agent, a siccative and an UV-stabilizer.

In accordance with a further aspect of the present invention, there has been provided a process for preparation of a composition comprising the step of mixing components (a)-(c) and at least one of components (d)-(f) as described above.

In accordance with a still further aspect of the present invention, there has been provided a process as described above, wherein the step comprises mixing the components with further components
  (g) at least one other biocide soluble in the diluent, and
  (h) at least one of a water-soluble or water-insoluble dye, a color pigment, an anti-corrosive agent, a siccative and an UV-stabilizer.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

It has been discovered that the objects of the present invention can be fulfilled by a composition for preservation of wood and wood-based materials, otherwise referred to as a wood preservative, comprising (a) 1-[[2-(2,4-dichloro-phenyl)-1,3-dioxolan-2-yl]methyl]-1H-1,2,4-triazole, (b) at least one compound selected from the group consisting of (i) cyano-(4-fluoro-3-phenoxyphenyl)-methyl-3-(2,2-dichloroethenyl)-2,2-dimethylcyclopropylcarboxylate, (ii) ((pentafluorophenyl)-methyl)-1R,3R-3-(2,2-dichloroethenyl)-2,2-dimethylcyclopropylcarboxylate, (iii) methyl-bisthiocyanate, (iv) N,N-dimethyl-N'-phenyl-N'-(fluorodichloromethylthio)sulfamide, (v) N,N-dimethyl-N'-p-tolyl-N'-(dichlorofluoro-methylthio)sulfamide, and (c) a suspending agent that comprises at least one of a diluent, an emulsifier and a wetting agent.

Optionally the wood preservative further comprises at least one of a group consisting of one other insecticide, a processing auxiliary or additive, an organic chemical binding agent, a fixative, a dye, and a pigment.

This composition possesses good activity against wood-destroying and wood-discoloring fungi and also against termites. It can be used in the form of a concentrate to be suitably diluted with a diluent prior to use, or can be used in a ready-to-use form, directly without dilution. Furthermore, the components of this composition can be present in the form of a kit or package, to be mixed by a user prior to use.

In a preferred embodiment, the wood preservative comprises:

0.001%-5% by weight, preferably
0.2%-2% by weight, of component (a) a compound 1-[[2-(2,4-dichloro-phenyl)-1,3-dioxolan-2-yl]methyl]-1H-1,2,4-triazole, and
0.001%-3% by weight, preferably
0.2%-2% by weight, of (b) at least one compound selected from the group consisting of cyano-(4-fluoro-3-phenoxyphenyl)-methyl-3-(2,2-dichloroethenyl)-2,2-dimethylcyclopropylcarboxylate, ((penta fluorophenyl)-methyl)-1R,3R-3-(2,2-dichloroethenyl)-2,2-dimethylcyclopropylcarboxylate, methyl-bisthiocyanate, N,N-dimethyl-N'-phenyl-N'-(fluorodichloromethylthio)sulfamide and N,N-dimethyl-N'-p-tolyl-N'-(dichlorofluoromethylthio)sulfamide, and
more than 75% by weight, preferably
more than 90% by weight, of component (c) a suspending agent comprising at least one of a diluent, an emulsifier and a wetting agent.

In accordance with one embodiment of the present invention, the diluent of component (c) comprises an organic chemical solvent or solvent mixture, preferably at least one polar, organic chemical solvent and/or an oily or oil-like low volatile organic chemical solvent, or a mixture of water and/or at least one organic chemical solvent, preferably at least one polar organic chemical solvent, and/or an oily or oil-like, low-volatility organic chemical solvent or solvent mixture and at least one emulsifier and/or wetting agent.

In accordance with another embodiment of the present invention a wood preservative comprises 0.1%-25% by weight, preferably 1%-18% by weight, solid, of at least one of components (d) a binding agent and (e) a fixative.

In accordance with another embodiment of the present invention, a weight ratio of binding agent, fixative and/or one of their mixtures to the diluent or diluent mixture and to the emulsifier or emulsifier mixture and/or wetting agent or wetting agent mixture contained in the agent or concentrate is 8.5:1 to 1:99.

The organic chemical binding agent or binding agent mixture can be partly replaced by component (f) at least one plasticizer.

In accordance with a preferred embodiment, a wood preservative comprises 0.001%-5% by weight, preferably
0.2%-2% by weight, of 1-[[2-(2,4-dichlorophenyl)-1,3-dioxolan-2-yl]methyl]-1H-1,2,4-triazole,
0 001%-3% by weight, preferably
0.2%-2% by weight, of at least one compound selected from the group consisting of cyano-(4-fluoro-3-phenoxyphenyl)-methyl-3-(2,2-dichloroethenyl)-2,2-dimethylcyclopropylcarboxylate, ((pentafluorophenyl)-methyl)-1R,3R-3-(2,2-dichloroethenyl)-2,2-dimethylcyclopropylcarboxylate, methyl-bisthiocyanate, N,N-dimethyl-N'-phenyl-N'-(fluorodichloromethylthio)sulfamide and N,N-dimethyl-N'-p-tolyl-N'-(dichlorofluoromethylthio)sulfamide and
0.1%-28% by weight, preferably
1%-18% by weight, (calculated as solid) of at least one organic chemical binding agent and/or fixative or plasticizer and a weight ratio of total content of organic chemical binding agent and/or fixative or plasticizer to total content of diluent (including solvent or solvent mixture and/or water and/or emulsifier and/or wetting agent) is
1:1.2 to 1:99, preferably
1:2 to 1:25.

According to another embodiment, the diluent of component (c) preferably comprises at least one organic chemical, low-volatility solvent having an evaporation number above 35 and a flash point above 30° C., preferably an oily or oil-like, organic chemical solvent or solvent mixture or contains one or more of these low volatile solvents.

According to a further embodiment of the present invention 0.5% to 23% by weight, preferably
2% to 15% by weight of the organic chemical, low volatile solvent or solvent mixture having a flash point above 30° C. is replaced by an equivalent amount of one or more organic chemical binding agents and/or fixatives, the organic chemical binding agents and/or fixatives employed being those which are dispersible or emulsifiable, but preferably soluble in the solvent or solvent mixture and the replacement being subject to the provision that the mixture obtained or the solvent mixture obtained likewise exhibits a flash point above 30° C. and the organic chemical solvent or solvent mixture is an oily or oil-like solvent.

In accordance with another preferred embodiment of the present invention, a ready-to-use agent for the preservation of wood and wood-based materials comprises 0.001%-5% by weight, preferably
0.2%-2% by weight, of component (a) a compound 1-[[2-(2,4-dichlorophenyl)-1,3-dioxolan-2-yl]methyl]-1H-1,2,4-triazole,
0.001%-3% by weight, preferably 0.2%–2% by weight, of component (b) at least one compound selected from the group consisting of cyano-(4-fluoro-3-phenoxyphenyl)-methyl-3-(2,2-dichloroethenyl)-2,2-dimethylcyclopropylcarboxylate, ((pentafluorophenyl)-methyl) -1R,3R-3-(2,2-dichloroethenyl)-2,2-dimethylcyclopropylcarboxylate, methyl-bisthiocyanate, N,N-dimethyl-N'-phenyl-N'-(fluorodichloromethylthio)sulfamide and N,N-dimethyl-N'-p-tolyl-N'-(dichlorofluoromethylthio)sulfamide, 0.1%–28% by weight, preferably 1%–18% by weight, of at least one of components (d) an organic chemical binding agent, and (e) a fixative, and component (f) a plasticizer, 0%–5% by weight, preferably 0.01%–4% by weight, of component (g) at least one of a biocide or biocide mixture soluble in the organic chemical solvent or solvent mixture, 0%–8% by weight, preferably 0.1%–4% by weight, of component (h) at least one of a water-soluble and water-insoluble dye, a color pigment, an anti-corrosive agent, a siccative, and an UV-stabilizer, and 99.899%–51% by weight, preferably 98.49%–70% by weight, of component (c) a diluent or diluent mixture comprising at least one organic chemical solvent or solvent mixture and/or water and/or at least one emulsifier and/or wetting agent or mixture thereof.

According to one embodiment, the composition of the present invention comprises 0.001%–5% by weight, preferably 0.2%–2% by weight, of component (a) a compound, 1-[[2-(2,4-dichlorophenyl)-1,3-dioxolan-2-yl]methyl]-1H-1,2,4-triazole, 0.001%–3% by weight, preferably 0.2%–2% by weight, of component (b) at least one compound selected from the group consisting of cyano-(4-fluoro-3-phenoxyphenyl)-methyl-3-(2,2-dichloroethenyl)-2,2-dimethylcyclopropylcarboxylate, ((pentafluorophenyl)-methyl)-1R,3R-3-(2,2-dichloroethenyl)-2,2-dimethylcyclopropylcarboxylate, methylbisthiocyanate, N,N-dimethyl-N'-phenyl-N'-(fluorodichloromethylthio)sulfamide and N,N-dimethyl-N'- p-tolyl-N'-(dichlorofluoromethylthio)sulfamide, and 2%–85% by weight, preferably 8%–40% by weight, (calculated as solid) of at least one of components (d) an organic chemical binding agent, (e) a fixative and (f) a plasticizer, and the weight ratio of total content of organic chemical binding agent and/or fixative or plasticizer to total content of diluent (including solvent or solvent mixture and/or water and/or emulsifier and/or wetting agent) is 8.5:1 to 1:48, preferably 1:1.45 to 1:11.5.

According to a preferred embodiment, the composition of the present invention comprises 0 001%–5% by weight, preferably 0.2%–2% by weight, of component (a) a compound, 1-[[2-(2,4-dichlorophenyl)-1,3-dioxolan-2-yl]methyl]-1H-1,2,4-triazole, 0.001%–3% by weight, preferably 0.2%–2% by weight, of component (b) at least one compound selected from the group consisting of cyano-(4-fluoro-3-phenoxyphenyl)-methyl-3-(2,2-dichloroethenyl)-2,2-dimethylcyclopropylcarboxylate, ((pentafluorophenyl)-methyl)-1R,3R-3-(2,2-dichloroethenyl)-2,2-dimethylcyclopropylcarboxylate, methyl-bisthiocyanate, N,N-dimethyl-N'-phenyl-N'-(fluorodichloromethylthio)sulfamide and N,N-dimethyl-N'-p-tolyl-N'-(dichlorofluoromethylthio)sulfamide, 2%–85% by weight, preferably 8%–1% by weight, of at least one of components (d) an organic chemical binding agent, (e) a fixative and (f) a plasticizer, 20%–0% by weight, preferably 8%–1% by weight, of one other fungicide or fungicide mixture soluble in the organic chemical solvent or solvent mixture and a diluent or diluent mixture as the remaining component, comprising at least one organic chemical solvent or solvent mixture or water and/or solvent or solvent mixture and/or at least one emulsifier and/or wetting agent or a mixture thereof. Optionally, at least one of a dye, a color pigment, an anti-corrosive agent, a siccative, and an UV-stabilizer can be added to the diluent.

In accordance with another embodiment of the present invention, a process for preparing the above-described compositions comprises a step of mixing components (a)–(c) with at least one of components (d)–(h) at a temperature of between −5° C. and 80° C., preferably between 15° C. and 45° C., and at a pressure between 400 mm Hg and 850 mm Hg (0.5332 to 1.1332 bar), preferably between 600 mm Hg and 790 mm Hg (0.7999 to 1.0532 bar).

The present invention is further described below by reference to the following examples.

EXAMPLE 1

A composition, for preservation of wood and wood-based materials, having termiticidal and fungicidal activities, and comprising the following components was made:

| | |
|---|---|
| 1-[[2-(2,4-dichlorophenyl)-1,3-dioxolan-2-yl]methyl]-1H-1,2,4-triazole (azaconazole) | 1% |
| cyano-(4-fluoro-3-phenoxyphenyl)-methyl-3-(2, 2-dichloroethenyl)-2, 2-dimethylcyclopropylcarboxylate (cyfluthrin) | 0.1% |
| dibutyl phthalate | 4.0% |
| spindle oil | 10.0% |
| white spirit (mixture of aliphatic and aromatic hydrocarbons) | 84.9% |

EXAMPLE 2

An azure-like wood preservative with termiticidal and fungicidal activities and comprising the following components was made:

| | |
|---|---|
| 1-[[2-(2,4-dichlorophenyl)-1,3-dioxolan-2-yl]methyl]-1H-1,2,4-triazole (azaconazole) | 0.35% |
| cyano-(4-fluoro-3-phenoxyphenyl)-methyl-3-(2,2-dichloroethenyl)-2,2-dimethyl-cyclopropylcarboxylate (cyfluthrin) | 0.1% |
| pigment | 0.5% |
| alkyd resin (70%) | 10.0% |
| anti-settling agent | 0.2% |
| siccative | 0.2% |
| white spirit (mixture of aliphatic | 88.65% |

-continued

| |
|---|
| and aromatic hydrocarbons) |

EXAMPLE 3

A wood preservative with termiticidal and fungicidal activities and comprising the following components was made:

| | |
|---|---|
| 1-[[2-(2,4-dichlorophenyl)-1,3-dioxolan-2-yl]methyl]-1H-1,2,4-triazole (azaconazole) | 0.35% |
| cyano-(4-fluoro-3-phenoxyphenyl)-methyl-3-(2,2-dichloroethenyl)-2,2-dimethyl-cyclopropylcarboxylate (cyfluthrin) | 0.05% |
| quaternary ammonium compounds | 1.7% |
| alkyd resin (70%) | 8.0% |
| emulsifier | 1.4% |
| water | 88.5% |

What is claimed is:

1. A composition for preservation of wood and wood-based materials comprising:
   (a) from about 0.001% to 5%, based on the total weight of all components, of a compound 1-[[2-(2,4-dichlorophenyl)-1,3-dioxolan-2-yl]methyl]-1H-1,2,4-triazole,
   (b) from about 0.001% to 3%, based on the total weight of all components, of at least one compound selected from the group consisting of
      (i) cyano-(4-fluoro-3-phenoxyphenyl)-methyl-3-(2,2-dichloroethenyl)-2,2-dimethylcyclopropyl-carboxylate, and
      (ii) ((pentafluorophenl)methyl)-1R,3R-3-(2,2-dichloroethenyl)-2,2-dimethylcyclopropylcarboxylate, and
   (c) a suspending agent selected from the group consisting of a diluent, an emulsifier, a wetting agent and mixtures thereof.

2. A composition as claimed in claim 1, wherein the amount of component (a) is from about 0.2 to 2%, and the amount of component (b) is from about 0.2 to 2%, in each case based on the total weight of all components.

3. A composition as claimed in claim 1, wherein the amount of component (c) is more than 75% of total weight of all components.

4. A composition as claimed in claim 1, wherein said diluent comprises at least one of an organic solvent and water, and said organic solvent comprises at least one of a polar solvent and an oily or oil-like low-volatility organic solvent.

5. A composition as claimed in claim 4, wherein said low-volatility organic solvent has an evaporation number above 35 and a flash point above 30° C.

6. A composition as claimed in claim 1, wherein the diluent of said component (c) comprises at least one of an organic solvent and water and said organic solvent comprises at least one of a polar solvent and an oily or oil-like low-volatility organic solvent.

7. A composition as claimed in claim 6, wherein said low-volatility organic solvent has an evaporation number above 35 and a flash point above 30° C.

8. A composition as claimed in claim 1, wherein said amount of organic solvent that is being replaced is from about 0.5% to 23% by weight of said solvent.

9. A composition as claimed in claim 1, wherein said composition further comprises at least one additional biocide soluble in said diluent.

10. A composition as claimed in claim 9, wherein the amount of said additional biocide is up to 5% and the amount of component (c) is from about 99.899% to 51% of total weight of all components.

11. A composition as claimed in claim 1, wherein said composition further comprises an amount of one other fungicide which is soluble in component (c).

12. A composition as claimed in claim 1, wherein said composition further comprises an amount of a fungicide which is soluble in component (c).

13. A composition as claimed in claim 12, wherein the amount of fungicide is not more than 20% of total weight of all components.

14. A process for preparation of a composition for the preservation of wood and wood based materials comprising the step of mixing
   (a) from about 0.001% to 5%, based on the total weight of all components, of a compound 1-[[2-(2,4-dichlorophenl)-1,3-dioxolan-2-yl]methyl]-1H-1,2,4-triazole,
   (b) from about 0.001% to 3%, based on the total weight of all components, of at least one compound selected from the group consisting of
      (i) cyano-(4-fluoro-3-phenoxyphenyl)-methyl-3-(2,2-dichloroethenyl)-2,2-dimethylcyclopropyl-carboxylate, and
      (ii) ((pentafluorophenyl)methyl)-1R,3R-3-(2,2-dichloroethenyl)-2,2-dimethylcyclopropylcarboxylate, and
   (c) a suspending agent selected from the group consisting of a diluent, an emulsifier, a wetting agent and mixtures thereof.

15. A composition as claimed in claim 1, wherein component (b) is cyano-(4-fluoro-3-phenoxyphenyl)-methyl-3-(2,2-dichloroethenyl)-2,2-dimethylcyclo-propylcarboxylate.

16. A composition as claimed in claim 1, wherein component (b) is ((pentafluorophenyl)-methyl)-1R,3R-3-(2,2-dichloroethenyl)-2,2-dimethylcyclopropylcarboxylate.

17. A composition as claimed in claim 1, comprising more than 75% by weight of component (c).

18. A composition as claimed in claim 1, comprising more than 90% by weight of component (c).

19. A composition as claimed in claim 1, consisting essentially of components (a), (b) and (c).

20. A composition as claimed in claim 1, wherein component (c) comprises an oily or oil-like, low-volatility organic solvent.

21. A composition as claimed in claim 1, additionally comprising dibutylphthalate.

22. A composition as claimed in claim 1, additionally comprising an alkyd resin binder.

23. A composition as claimed in claim 21, additionally comprising an alkyd resin binder.

* * * * *